(12) United States Patent
Poletto

(10) Patent No.: US 8,457,749 B2
(45) Date of Patent: Jun. 4, 2013

(54) MODULATION OF TRIGEMINAL REFLEX STRENGTH

(75) Inventor: Christopher Poletto, North Oaks, MN (US)

(73) Assignee: Medtronic, Inc., Minneapolis ( * ) Notice: Subject to any disclaimer, the term of this patent is extended or adjusted under 35 U.S.C. 154(b) by 89 days.

(21) Appl. No.: 13/078,976

(22) Filed: Apr. 3, 2011

(65) Prior Publication Data

US 2011/0264167 A1    Oct. 27, 2011

Related U.S. Application Data

(60) Provisional application No. 61/326,772, filed on Apr. 22, 2010.

(51) Int. Cl.
*A61N 1/18*    (2006.01)

(52) U.S. Cl.
USPC ............................................................ 607/46

(58) Field of Classification Search
USPC .................................................. 607/43–47
See application file for complete search history.

(56) References Cited

U.S. PATENT DOCUMENTS

| 5,061,234 A | 10/1991 | Chaney et al. |
| 7,684,858 B2 | 3/2010 | He et al. |
| 2004/0138097 A1 | 7/2004 | Guyuron |
| 2006/0149337 A1 | 7/2006 | John |

*Primary Examiner* — Rex R Holmes

(57) ABSTRACT

A method includes evoking and recording the response of a trigeminal reflex in the presence and absence of occipital nerve stimulation (ONS) to determine whether, and to what extent, ONS modulates the trigeminal reflex. If the ONS modulates the trigeminal reflex, e.g. to a sufficient degree, the subject may be considered a candidate for ONS for treatment of headache.

16 Claims, 7 Drawing Sheets

MODULATION OF TRIGEMINAL REFLEX STRENGTH

The present application claims priority to U.S. Provisional Patent Application No. 61/326,772, filed Apr. 22, 2010, which application is hereby incorporated by reference as if re-written in its entirety.

FIELD

The present disclosure relates generally to use of implantable electrical signal generators for application of electrical signals to nerves; particularly to such use for determining the ability of signals applied to an occipital nerve to affect trigeminal reflexes.

BACKGROUND

Application of electrical signals to occipital nerves (occipital nerve stimulation or "ONS") via implantable electrical signal generators has been shown to be effective in treatment of chronic migraine in some patients and has potential for treatment of other types of headache. While promising, initial studies have shown that only about 40% of patients with medically refractory chronic migraine receive benefits from ONS. Improving this responder rate through patient screening would be beneficial to the patient. That is, a patient who is not a viable candidate could avoid an unnecessary procedure and surgery associated with implantation of an electrical medical device system. One method that has been used to screen candidates for ONS employs a trialing system that includes a percutaneously inserted lead and an externalized electrical signal generator. Although this practice is common, it does not appear to have a high positive predictive value as to whether the patient will respond to ONS via an implantable system.

The exact mechanism of how ONS treats migraine is not well understood. It is believed that many types of headache are associated with nociceptive pathways of the trigeminal nerve and that the therapeutic effect of ONS may be due to convergence of occipital afferents and trigeminal afferents in the lower brain stem/upper cervical region, such as the trigeminal cervical complex. Via this convergence. ONS may have an inhibitory effect on nociception transmitted via trigeminal afferents, which may then have a pain-relieving effect on migraine or other types of headache.

SUMMARY

This disclosure, among other things, describes methods for using the presence or strength of modulation of a trigeminal reflex as an indicator of likelihood of positive therapeutic outcome from ONS for various types of headache, including chronic migraine. While not intending to be bound by theory, it is believe that ONS for headache works by inhibiting pain signals originating in the trigeminal nerve through direct and indirect connections in the trigeminal cervical complex (TCC). Many of the methods described herein use reflexes that also involve trigeminal connections in the TCC to gauge the strength of the connections between the occipital nerve (e.g., the greater occipital nerve) and the trigeminal pain pathways. Again, without intending to be bound by theory, it is believed that the stronger the modulatory effects of ONS on the trigeminal reflexes, the more likely ONS will provide clinical benefit in patients suffering from headache.

Testing the effects of occipital nerve stimulation on trigeminal reflexes can be done quickly in a relatively non-invasive manner. While ONS trialing using an external electrical signal generator is not very invasive, the trialing typically occurs over several days, and can present some difficulties for those undergoing such trialing. The ability to maintain the position of the leads during the entire time of the trial can also be difficult, and lead migration can affect the ability to determine whether the trialing is truly predictive of an outcome that may be achieved with an implantable ONS system. Further, trialing with an external signal generator may be likely to be subject to placebo effects. Many of these problems may be alleviated with the methods described herein, which involve testing the effect of ONS on a trigeminal reflex.

In various embodiments, a method described herein includes applying electrical signals to an occipital nerve of a subject during a first period of time; applying a first reflex-initiating stimulus to a trigeminal nerve of the subject during first the period of time; and recording a first response of a muscle associated with the reflex during the first period of time. The application of occipital nerve stimulation may precede the measurement of the reflex response or it may coincide with it. The application of electrical signals to an occipital nerve may utilize electrodes on an indwelling lead or may utilize transdermal stimulation from electrodes applied to the skin. The method further includes applying a second reflex-initiating stimulus to the trigeminal nerve of the subject during a second period of time in which electrical signals are not being applied to the occipital nerve; and recording a second response of the muscle associated with the reflex during the second period of time. The method also includes determining whether the application of the electrical signals to the occipital nerve affected the trigeminal reflex response, which includes comparing the first response to the second. The first and first and second reflex-initiating stimuli preferably consist of, or consist essentially of, the same parameters. The method may be used to identify or select subjects as candidates for occipital nerve stimulation therapy if the application of the electrical signals to the occipital nerve are determined to have affected the trigeminal reflex response. The first and second periods of time may be in any order and may be repeated to improve the ability to detect reflex modulation.

In some embodiments, a method for determining the strength of modulation of a trigeminal reflex by occipital nerve stimulation in a subject suffering from headache includes identifying the subject suffering from headache and applying electrical signals to an occipital nerve of the subject during a first period of time. The method further includes evoking a first trigeminal reflex in the subject during the first period of time, and recording a first response to the evoked first reflex. The method also includes evoking a second trigeminal reflex in the subject during a second period of time in which electrical signals are not applied to the occipital nerve, and recording a second response to the evoked second reflex. The method additionally includes determining the strength of the modulation of the trigeminal reflex by the occipital nerve stimulation by comparing one or more parameters of a characteristic reflex response of the first recorded response to one or more parameters of a characteristic reflex response of the second recorded response.

In many embodiments, a method for selecting a subject suffering from headache as a candidate for receiving occipital nerve stimulation therapy includes monitoring a trigeminal reflex response of the subject in the presence and the absence of occipital nerve stimulation and determining whether the occipital nerve stimulation affected a parameter of a characteristic aspect of a trigeminal reflex response by at least a predetermined amount. The determination includes comparing the response in the presence of the occipital nerve stimulation to the response in the absence of the occipital nerve stimulation. The method further includes selecting the subject as a candidate for occipital nerve stimulation therapy if the occipital nerve stimulation affected the parameter of the characteristic trigeminal reflex response by at least the predetermined amount.

In addition to the various advantages described above, other advantages of one or more embodiments of the methods and systems described herein will be apparent to those of skilled in the art upon reading the following detailed description.

BRIEF DESCRIPTION OF THE DRAWINGS

The accompanying drawings, which are incorporated into and firm a part of the specification, illustrate several embodiments of the present disclosure and, together with the description, serve to explain the principles of the disclosure. The drawings are only for the purpose of illustrating embodiments of the disclosure and are not to be construed as limiting the disclosure.

In FIG. 2A, the diagram indicates an absence of occipital nerve stimulation. In FIG. 2B, the diagram indicates an presence of occipital nerve stimulation.

Figure 1A:
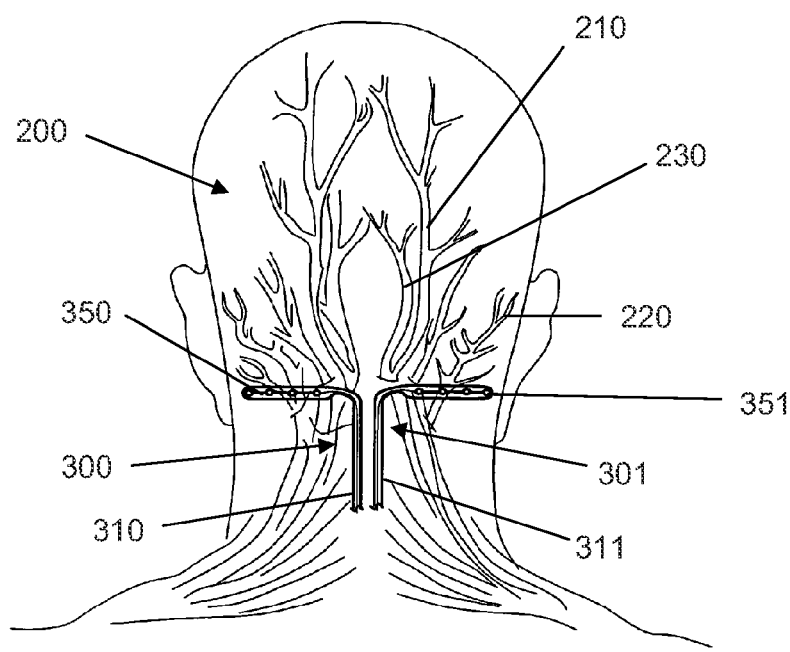
FIGS. 1A-B are schematic drawings illustrating embodiments of portions of leads implanted in a subject in a position suitable for applying electrical signals to an occipital nerve.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

"Exemplary" or "representative" is used herein in the sense of "for example" or "for the purpose of illustration", and not in a limiting sense.

In the context of the present disclosure, the terms "treat", "therapy", and the like mean alleviating, slowing the progression, preventing, attenuating, or curing the treated disease.

As used herein, a "subject" is an animal having an occipital nerve and a trigeminal nerve. Typically a subject is a mammal. Most often the subject will be a human; particularly a human suffering from headache.

As used herein, a subject "suffering from headache" is a subject who has a history of having headaches and who is likely to have headaches in the future. For example, a person suffering from migraine is a person who is like to have a migraine headache in the future. The subject need not be actually suffering from a headache at a particular time in question.

As used herein, "occipital nerve stimulation" means the application of electrical signals to an occipital nerve. Similarly, "stimulation of an occipital nerve" means application of an electrical signal to the occipital nerve. The electrical signals may be applied via one or more electrodes operably coupled to an electrical signal generator, such as a pulse generator or a neurostimulator device. Such electrical signal generators may be implantable for the purpose of delivering long term therapy. For trialing purposes (e.g., to determine whether a subject may be a suitable candidate for long term implantable therapy) the signal generator is typically external to the patient. While the term "stimulation" is used, the electrical signals applied to the nerve do not necessarily result in "stimulation" of the nerve. Such signals are typically delivered in pulses having a pulse width, amplitude, and frequency. The stimulating electrodes themselves may reside under the skin or may be electrically coupled to the skin.

A "nerve", as used herein, includes ay trunk, branch, or sub-branch of the nerve. For example, the occipital nerve includes the greater occipital nerve, the lesser occipital nerve, and the third occipital nerve.

Application of an electrical signal "to a nerve", as used herein, means that the applied electrical signal affects the nerve. It will be understood that an electrode need not be placed in direct contact with a nerve to deliver a signal from the electrode to the nerve. Rather, the electrode may be placed in sufficiently close proximity to the nerve such that the nerve falls within the range of an electrical field generated by the electrode (and any other electrodes involved in generating the electrical field).

Application of a stimulus "to a nerve", whether the stimulus is an electrical signal, heat, or other stimulus, similarly means that the applied stimulus affects the nerve. The stimulus need not be applied directly to the nerve. For example a reflex-initiating stimulus may be applied to the nerve, an area innervated by the nerve, in proximity to the nerve, or to the subject in any manner to evoke the intended reflex.

As used herein, a "reflex-initiating stimulus" is a stimulus sufficient to evoke the intended reflex or sufficient to reproducibly (i.e., greater than 99% of the time) evoke the intended reflex in a population of healthy subjects having no discernable abnormalities with the reflex. A reflex-initiating stimulus may not evoke the reflex or a characteristic aspect of the reflex in subjects suffering from a medical condition that may affect the reflex, such as with headache and a trigeminal reflex, or when the subject is undergoing a procedure that may affect the reflex, such as with occipital nerve stimulation and a trigeminal reflex.

As used herein, a "characteristic aspect" of a trigeminal reflex means an aspect that is typically observed in healthy subjects having no discernable abnormality associated with the reflex. For example, electromyographic recordings of the orbicularis oculi muscle typically show a bimodal response to evoking the blink reflex (e.g., application of a reflex-initiating stimulus to the supraorbital nerve) with an early phase (R1) and a late phase (R2) response. Other trigeminal reflex responses also have characteristic aspects that are well know in the art.

This disclosure, among other things, relates to determining whether occipital nerve stimulation modulates a trigeminal reflex response in a given subject, particularly a subject suffering from headache. In various embodiments, if such modulation occurs or if the modulation is of a sufficient degree, the subject suffering from headache may be considered a candidate for occipital nerve stimulation therapy that employs an implantable electrical signal generator. In most cases, occipital nerve stimulation includes use of an electrical signal generator external to the subject for the purpose of determining whether the stimulation modulates a trigeminal response or whether a patient is a suitable candidate for implantable occipital nerve stimulation therapy.

Any suitable electrical signal generator system may be employed for the purposes of providing stimulation to the occipital nerves, whether for long term therapy or for purposes of trialing or testing. An example of an external electrical signal generator that may be employed for stimulating occipital nerves is the Medtronic, Inc. Model 37022 External Neurostimulator. Implantable electrical signal generators that may be employed include Medtronic, Inc.'s Restore® or Synergy® series of implantable neurostimulators.

With such systems, a lead is typically employed to deliver the signals generated from the device to the occipital nerve of a subject. A lead includes a distal end portion having one or more electrodes and a proximal end portion having one or more contacts for electrically coupling with the electrical signal generator device. Conductors run the length of the lead and typically electrically couple discrete electrodes to discrete contacts. Thus, a signal generated by the signal generator may be transferred to the subject via the electrodes by way of the contacts and the conductors.

For purposes of trialing, screening, or testing, the distal portion of the lead may be implanted in the subject such that the electrodes are positioned in proximity to the occipital nerve and are capable of delivering electrical signals to the occipital nerve. Alternately, the distal portion of the lead may be applied to the outside of the subject's skin with the electrodes electrically coupled to the skin. The proximal portion of the lead may be external to the patient and may be operably coupled to an external trial signal generator. For purposes of long-term implantable therapy, the distal portion of the lead may be placed in proximity to the occipital nerve and the proximal portion may be tunneled subcutaneously and coupled with an implanted electrical signal generator.

Figure 1B:
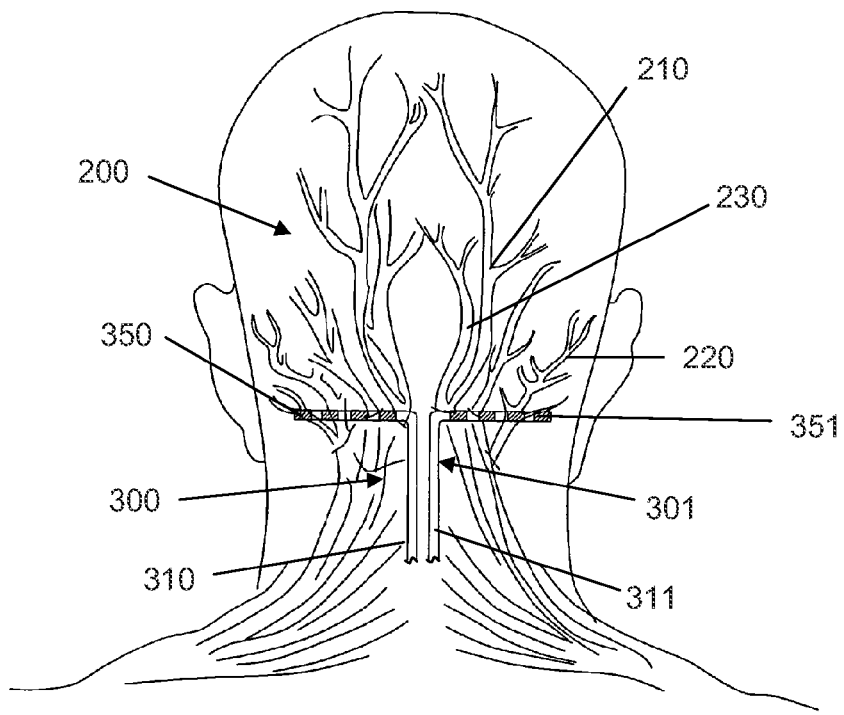

Referring now to FIGS. 1A-B, portions of leads 300, 301 are shown implanted in a subject to provide electrical signals to left and right occipital nerves 200. As used herein, occipital nerve 200 includes the greater occipital nerve 210, the lesser occipital nerve 220 and the third occipital nerve 230. The greater and lesser occipital nerves are spinal nerves arising between the second and third cervical vertebrae (not shown). The third occipital nerve arises between the third and fourth cervical vertebrae. The portion of the occipital nerve 200 to which an electrical signal is to be applied may vary depending on the disease to be treated and associated symptoms, the reflex to be tested, or the stimulation parameters to be applied. In various embodiments, the lead distal portions 350, 351 that contain electrodes are placed to allow bilateral application of electrical signals to the occipital nerve 200 at a level of about C1 to about C2 or at a level in proximity to the base of the skull. The position of the electrode(s) may vary. It will be understood that the electrode need not, and in various embodiments preferably does not, contact the nerve to apply the signal to the nerve. It will be further understood that a signal may be applied to any suitable portion of an occipital nerve, whether at a trunk, branch, or the like. In various embodiments, one or more electrodes are placed between about 1 cm and about 8 cm from the midline to effectively provide an electrical signal to the occipital nerve 200. It will be further understood, that one or the other of the left or right occipital nerve 200 may be stimulated in some embodiments, and both need not be stimulated in all embodiments.

As shown in FIG. 1A, a lead 300, 301 may include a paddle shaped distal portion 350, 351 containing electrodes (not labeled). Such paddle shaped leads are often referred to as surgical leads. Examples of surgical leads that may be used or modified to form leads as described herein include Medtronic Inc.'s Resume, SymMix, On-Point, or Specify series of leads. Surgical leads typically contain electrodes that are exposed through one face of the paddle, providing directional stimulation. The depicted leads 300, 301 also include proximal portions 310, 311 for coupling signal generator (not shown). The leads 301), 301 may be coupled to the signal generator via a lead extension, screener cable, or the like (not shown).

As shown in FIG. 1B, the lead 300, 301 may include a distal portion 350, 351 that includes electrodes (not labeled) that are generally cylindrically shaped. Such leads are often referred to as percutaneous leads. Examples of percutaneous leads that may be used or modified to form leads as described herein include Medtronic Inc.'s Quad Plus, Pisces Quad, Pisces Quad Compact, or 1×8 SubCompact, 1×8 Compact, and 1×8 Standard leads. Such percutaneous leads typically contain ring electrodes that apply an electrical stimulation signal to tissue in all directions around the ring. Accordingly, the amplitude of the signal (and thus the energy required from the signal generator) applied may be greater with percutaneous leads than surgical leads for occipital nerve therapies, screening, trialing, and testing.

For purposes of trialing or screening, it may be desirable to place the distal portion of the lead, and thus the electrodes, in a location as close as practicable to the location in which electrodes would be placed if long-term implantable therapy were delivered. This should maximize the predictive effect of the screening or trialing. It may also be desirable for the stimulation parameters to be the same or similar for purposes of trialing, screening or testing as they would be if used for long-term implantable therapy.

Any combination of electrical signal parameters may be used for purposes of occipital nerve stimulation. In various embodiments, the pulse width of an electrical signal for occipital nerve stimulation is within the range of about 10 microseconds to about 600 microseconds; e.g., between about 90 microseconds to about 500 microseconds, or between about 300 microseconds to about 500 microseconds.

In various embodiments, the frequency of an electrical signal for occipital nerve stimulation is in the range of about 1 Hz to about 120 Hz; e.g., between about 5 Hz to about 50 Hz, or between about 5 Hz to about 20 Hz. In various embodiments, the amplitude of an electrical signal for occipital nerve stimulation is within the range of about 1 mA to about 20 mA; e.g., between about 5 mA to about 15 mA, or between about 8 mA to about 12 mA. It will be understood that the electrical signal may include a voltage parameter rather than a current parameter. The voltage of an electrical signal with for occipital nerve stimulation may be, e.g., in the range of about 0.1 mV to about 30 V, about 1 V to about 20 V, or about 5 V to about 10 V. The duration of a given sequence of electrical signals for occipital nerve stimulation may be any duration to achieve a desired effect. Non-limiting examples of durations for which stimulation signals may be applied to an occipital nerve include the range between about 10 minutes and about 10 hours, the range between about it hour and about 6 hours, and the range between about 2 hours and about 4 hours.

The results of short-term stimulation therapy with an externalized electrical signal generator and partially implanted leads has not proved to be very effective at predicting how a patient will respond to long-term therapy via an implantable system. Why such trailing is not very predictive is not well understood. Perhaps false positives are observed due to the placebo effect or the power of wishful thinking. Perhaps false negative results occur due to migration of the distal portion of the lead during trialing. Whatever the reason, alternative methods for screening or selecting candidates suffering from headache for occipital nerve stimulation therapy may prove useful.

A working hypothesis presented in this disclosure is that the strength of the connection between the occipital nerves and the trigeminal system can be measured and may used to predict whether a subject suffering from headache will respond to occipital nerve stimulation therapy. It is believed that most categories of headache involve sensory pain input via the trigeminal nerve. Such headaches include migraine headaches, cluster headaches, hemicrania continua headaches, and the like. While any of such headaches could theoretically be treated by occipital nerve stimulation therapy, only the more severe or intractable headaches, such as chronic migraine or chronic cluster headaches, are likely to be treated with occipital nerve stimulation therapy employing an implantable device due to the cost and invasiveness of the devices and procedures involved in such therapies.

It is further believed that occipital nerve stimulation therapy has an inhibitory effect on pain, nociception, the perception of pain, or the perception of nociception associated with sensory pathways involving the trigeminal system. Some of the sensory nociceptive pathways of the trigeminal nerve run through an area that overlaps caudal regions of the brain stem and upper cervical regions of the spinal cord, e.g., in the spinal trigeminal nucleus. As the occipital nerve arises from upper cervical regions, there may be some direct or indirect connections within the area of overlap between the two systems.

Figure 2A:
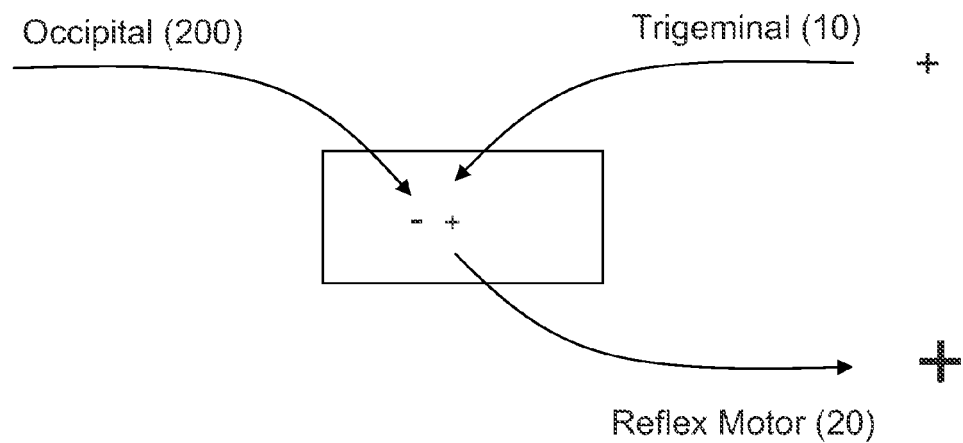
FIGS. 2A-B are schematic diagrams illustrating how occipital nerve stimulation may affect a trigeminal reflex.
Figure 2B:
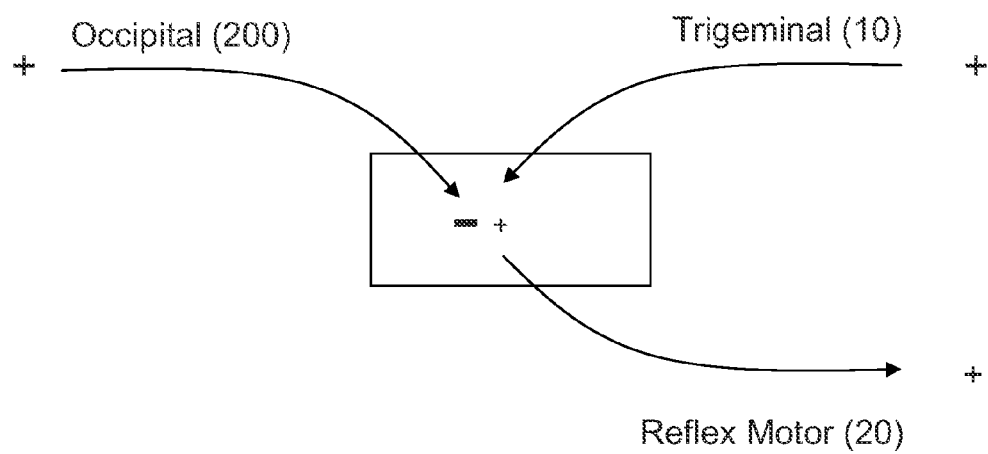

As described herein, one way to test the presence or strength of the connection between the trigeminal system and the occipital nerve in a given subject, and thus predict the potential for occipital nerve stimulation for treating headache in the subject, is to test the effect of occipital nerve stimulation on trigeminal reflexes. For example and with reference to FIGS. 2A-B, activation of trigeminal afferents (10), such as sensory nociceptive neurons, can result in activation of reflex motor neurons (20) and a concomitant changes in muscle activity, which can be recorded via electromyography (EMG). EMG activity following application of a reflex-inducing stimulus to a trigeminal nerve (10) can be recorded in the absence (FIG. 2A) and presence (or just after the presence) (FIG. 2B) of occipital nerve stimulation. As shown in the depicted drawings, it is believed that stimulation of the occipital nerve (200) will result in inhibition of the trigeminal reflex pathways and thus inhibition of some aspect of EMG activity in the muscle innervated by the reflex motor neurons (20). However, it is possible that occipital nerve stimulation may activate some aspect of the EMG activity associated with the trigeminal reflex. In either case, a connection and the relative strength of the connection between the trigeminal nerve and the occipital nerve in a given subject may be determined using the teachings presented herein.

Generally EMG activity associated with a trigeminal reflex exhibits characteristic activity. For example, the response may be uni-, bi- or higher-modal, with each mode having an amplitude, time of onset, duration, and the like. Thus the ability to inhibit the reflex response via occipital nerve stimulation may be observed in a decrease in amplitude, a delayed onset or a shorter duration of the EMG response, depending on the reflex. It will be understood that in the case of some trigeminal reflex EMG responses a lesser decrease in amplitude may be considered an indication of an inhibitory effect. For example, in reflexes that involve the inhibition of muscle activity (with baseline being active muscle contraction), e.g. the masseter inhibitory reflex, less of a decrease in EMG amplitude in response to a reflect-initiating response may be indicative of inhibition of the reflex by the occipital nerve stimulation.

The response to any trigeminal reflex, whether in the presence or absence of occipital nerve stimulation, may be recorded. The reflex can be evoked by applying a stimulus to any suitable branch or truck of the trigeminal nerve and the response may be recorded in any suitable reflex response muscle. Some of the well-known trigeminal reflexes that may be investigated include the blink reflex, the masseter inhibitory reflex, the corneal reflex, and the jaw-jerk reflex, each of which will be discussed below in more detail.

As used herein, a trigeminal nerve (also referred to a cranial nerve V or the fifth cranial nerve) includes any trunk, branch, or sub-branch of the trigeminal nerve. For example, the trigeminal nerve has three main sensory branches—the ophthalmic branch (also referred to as $V_1$), the maxillary branch (also referred to as $V_2$), and the mandibular branch (also referred to as $V_3$) which leave the skull through three separate foramina—the superior orbital fissure, the foramen rotundum, and the foramen ovale, respectively. The ophthalmic nerve carries sensory information from the scalp, the forehead, the upper eyelid, the conjunctiva of the eye, cornea, the nose, the nasal mucosa, the frontal sinuses and parts of the memengies. The maxillary nerve carries sensory information from the lower eyelid, the cheek, the nares, the upper lip, the upper teeth, the upper gums, the nasal musosa, the palate, the roof of the pharynx, the maxillary, the ethmoid sinuses, the shpenois sinuses, and parts of the menengies. The mandibular nerve carries sensory information form the lower lip, the lower teeth and gums, the chin, the jaw, parts of the ear, and parts of the menengies.

Examples of subbranches of the trigeminal nerve include the mental nerve and the supraorbital nerve. The mental nerve is a general somatic afferent nerve that provides sensation to the anterior aspects of the chin, lower lip, the buccal gingivae of the mandibular anterior teeth, and the premolars. It is a branch of the posterior trunk of the inferior alveolar nerve, which is itself a branch of the mandibular division of the trigeminal nerve. The supraorbital nerve is a terminal branch of the frontal nerve, which is the largest branch of the ophthalmic division of the trigeminal nerve. The supraorbital nerve passes through the supraorbital foramen, and innervates the upper eyelid, the conjunctiva of the eye, the frontal sinus, and the skin from the forehead extending back to the middle of the scalp.

Any suitable stimulus may be applied to a trigeminal nerve to evoke a trigeminal reflex. For example, an electrical signal, heat, or physical impact may be applied to provide the stimulus. It will be understood that the stimulus need not be applied directly to the nerve to evoke the response. Electrical signals may be applied via an electrode placed at or near (e.g., on the surface of the skin in proximity to) the nerve. An electrical signal generator, such as a pulse generator, may be used to deliver the signal to the electrode, which then delivers the signal to the nerve. The electrical signal may have any suitable parameters. In some embodiments, the signals are configured to stimulate nociceptive neurons of the nerve. Any suitable heat stimulus may be used to initiate the reflex. For example, heat may be delivered to the skin in proximity to the nerve via an IR laser, such as a yttrium aluminium garnet (YAG) infrared laser. Any suitable impact may be applied to evoke a trigeminal reflex. For example, a tap with fingers, a hand, a rubber mallet, or the like may be used to evoke one or more trigeminal reflexes.

While it may not be necessary, it may be desirable to stimulate nociceptive neurons. In some cases the reflex will be evoked without nociception. However, as trigeminal nociception is considered to play a significant role in headache, it may be desirable to stimulate trigeminal nociceptive neurons to determine which subjects may be good candidates for occipital nerve stimulation for treatment of headache.

Any suitable reflex response may be measured or recorded. Generally, EMG responses of the reflex muscles serve as a sensitive measure in which subtle differences can be detected. Any suitable method for measuring an EMG may be used. Typically, a recording electrode is placed in or near (e.g., on the surface of the skin in proximity to) the muscle. Any suitable electromyography may be used. For example, a Metron Clinical EMG Dual Channel Electromyograph, a Teca Te42 Electromyograph, or the like may be used.

A change in response (e.g., amplitude, onset or duration) of one or more characteristic aspects of the trigeminal reflex during a time in which occipital nerve stimulation is applied may be considered indicative of an operable coupling between the occipital nerve and the trigeminal nerve or pathways associated therewith. In most cases, a decrease in amplitude, a delayed onset or a decreased duration will be indicative of favorable couple for purposes of occipital nerve stimulation for treatment of headache. However, it may be desirable to quantify the differences in the response in the presence and absence of occipital nerve stimulation to gauge the strength of the coupling of the occipital nerve and the trigeminal nerve or pathways associated therewith. A cutoff or threshold with regard to the strength may be employed to determine whether a subject would be a suitable candidate for occipital nerve stimulation for treatment of headache. For example, if occipital nerve stimulation results in a 10% or greater change, a 15% or greater change, a 20% or greater change, a 25% or greater change or a 30% or greater change in a parameter of a characteristic aspect of a trigeminal reflex, the subject may be considered to be a candidate for occipital nerve stimulation for purposes of treating headache. Any suitable characteristic of a trigeminal response may be used for purposes of determining whether such thresholds are met. For example, the blink reflex has a characteristic bimodal EMG response having an early component designated R1 and a late component designated R2, and the masseter inhibitory reflex has a characteristic bimodal EMG response having an early component designated SP1 and a late component designated SP2 (see, e.g., Jens Ellrich, "Brain stem reflexes: Probing human trigeminal nociception," News Physiol. Sci., 15: 94-97, April 2000; and G. Cruccu, et al., "Idiopathic and symptomatic trigeminal pain," Journal of Neurology, Neurosurgery, and Psychiatry, 53:1034-1042, 1990). By way of further example, the corneal reflex and the jaw-jerk reflex have characteristic unimodal responses (see, e.g., G. Cruccu, et al., supra). Of course, any other characteristic aspect of a trigeminal nerve may be used for purposes of determining whether occipital nerve stimulation affects a trigeminal reflex and the extent to which occipital nerve stimulation affects a trigeminal reflex.

Any suitable trigeminal reflex may be tested or analyzed to determine the presence or strength of coupling of the trigemincal and occipital nerves. For example, the blink reflex, the masseter inhibitory reflex, the corneal reflex, the jaw-jerk reflex, or the like may be tested or analyzed. For purposes of example, some of these representative reflexes are described in more detail below.

The blink reflex involves a sensory-motor pathway from supraorbital nerve, which is a terminal branch of the frontal nerve, which is the largest branch of the ophthalmic division of the trigeminal nerve through the facial nerve (cranial nerve VII), which innervates the orbicularis oculi muscle. Thus, the blink reflex can be evoked by applying a reflex initiating stimulus to (e.g., at or near) the supraorbital nerve and can be recorded via the response at (e.g., in or near) the orbicularis oculi muscle. Any suitable stimulus may be applied. For example, an electrical signal may be applied via one or more surface electrodes placed at or near the supraorbital foramen or IR light of, for example, 2 micrometer wavelength and 3 millisecond duration may be applied to the supraorbital nerve area, e.g. as described in Jens Ellrich, supra, and references cited therein, or G. Cruccu et al., supra and references cited therein.

Figure 3A:
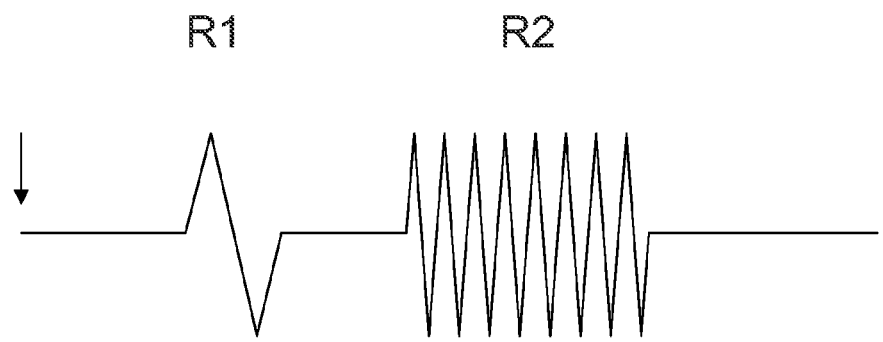
FIGS. 3A-C are schematic drawings of theoretical electromyographic recordings of the orbicularis oculi muscle following evoking of the blink reflex in the absence (A) and presence (B, C) of occipital nerve stimulation.
Figure 3B:
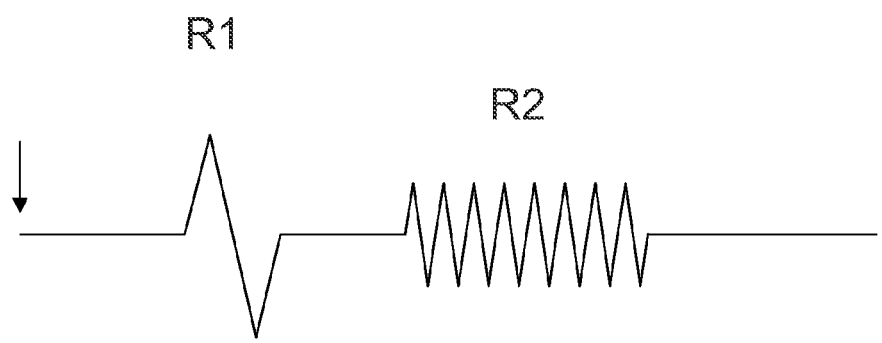
Figure 3C:
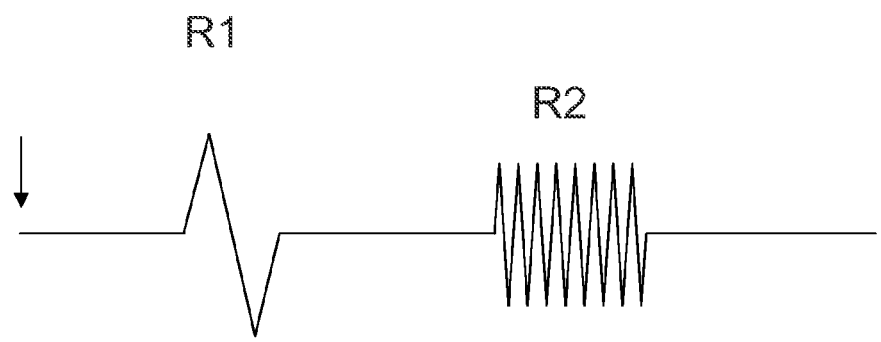

Referring now to FIGS. 3A-C, schematic drawings of examples of electromyographs a blink reflex response measured at the orbicularis oculi muscle are depicted. For purposes of example, FIG. 3A can be considered to represent a typical blink reflex response without concomitant occipital nerve stimulation, and FIGS. 3B-C can be considered some representative possibilities of a blink reflex response with concomitant occipital nerve stimulation in a subject in which there is a coupling of the occipital nerve and the trigeminal nerve or pathways associated therewith. The arrows depicted in FIGS. 3A-C indicate the timing of application of a reflex-initiating stimulus to the supraorbital nerve The x-axis represents amplitude, and the y-axis represents time.

As shown in FIG. 3A, the blink reflex typically includes an early phase response (contraction of the orbicularis oculi muscle), R1, and a later phase response (contraction of the orbicularis oculi muscle), R2. It is possible that the late R2 response, but not the early R1 response, is indicative of a nociceptive trigeminal pathway (see, e.g., Jens Ellrich, supra). Accordingly, it may be desirable to monitor the R2 response to determine whether a subject may be a good candidate for occipital nerve stimulation for treatment of headache. That is, as it is believed that nociceptive trigeminal neurons are involved in headache, the effect of occipital nerve stimulation on reflex pathways involving nociceptive trigeminal neurons may be predictive of the ability of a subject suffering from headache to respond to occipital nerve stimulation. However, the early R1 response appears to be affected in patients suffering from headache (see, e.g., G. Cruccu, et al., supra), and thus changes in R1 should also serve as valuable predictive indicators of occipital nerve stimulation for treatment of headache.

In FIG. 3B, the amplitude of the late R2 response is shown to be decreased relative to the R2 response in FIG. 3A. As discussed above, the response in FIG. 3B is an example of a response that might be seen with occipital nerve stimulation during the period of time in which the EMG response to the blink reflex is recorded. Such a decrease in amplitude of the R2 response would be indicative of coupling between the occipital nerve and the trigeminal nerve or pathways associated therewith that may be predictive of whether the patient would be a good candidate for occipital nerve stimulation for treatment of headache.

FIG. 3C provides another example of a response that may be indicative of a subject being a suitable candidate for occipital nerve stimulation for treatment of headache, where the time of onset of the R2 response is delayed, the duration of the R2 response is decreased, and the amplitude of the R2 response is decreased relative to that depicted in FIG. 3A. It will be understood that any suitable parameter (e.g., onset, duration, or amplitude) of any suitable characteristic aspect (e.g., R1 or R2) of the blink reflex may be employed for purposes of evaluating the existence or strength of coupling between the occipital nerve and the trigeminal nerve or pathways associated therewith or for determining whether a subject may be a suitable candidate for occipital nerve stimulation for treatment of headache.

The masseter inhibitory reflex involves a sensory-motor pathway from the mental nerve, which is a branch of the posterior trunk of the inferior alveolar nerve, which is a branch of the mandibular division of the trigeminal nerve, through motor aspects of the trigemical nerve, which innervate the masseter muscle. To test the masseter inhibitory reflex or the effect of occipital nerve stimulation on the masseter inhibitory reflex, a subject may clench their teeth or hold something between their teeth, a reflex-initiating stimulus may then be applied to (e.g., at or near) the mental nerve, and the response may be recorded via (e.g., in or near) the masseter muscle, in the case of the masseter-inhibitory reflex, the masseter muscle is contracted prior to evoking the reflex, and the reflex causes relaxation of the muscle. Thus, a lessened decrease in amplitude as a result of the reflex during occipital nerve stimulation (relative to no occipital nerve stimulation) may indicate that the subject is a good candidate for occipital nerve stimulation for headache.

Any suitable stimulus may be applied for evoking the masseter inhibitory reflex. For example, an electrical signal may be applied via one or more surface electrode placed at or near the mental foramen or IR light of, for example, 2 micrometer wavelength and 3 millisecond duration may be applied to the mental nerve area, e.g. as described in Jens Ellrich, supra, and references cited therein, or G. Cruccu et al., supra and references cited therein.

Figure 4A:
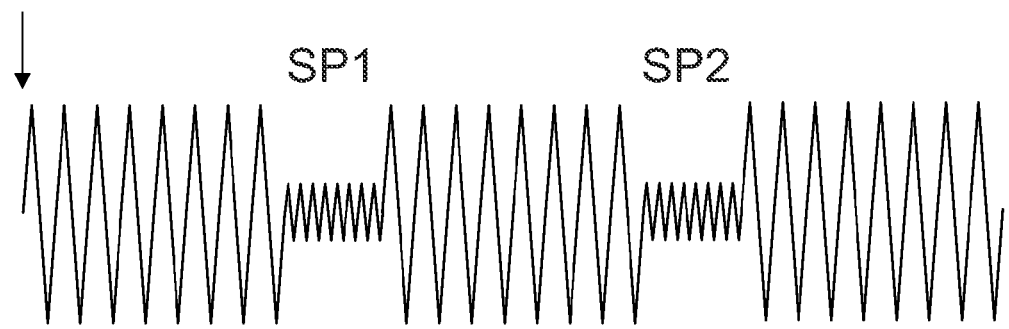
FIGS. 4A-B are schematic drawings of theoretical electromyographic recordings of the masseter muscle following evoking of the masseter inhibitory reflex in the absence (A) and presence (B) of occipital nerve stimulation.
Figure 4B:
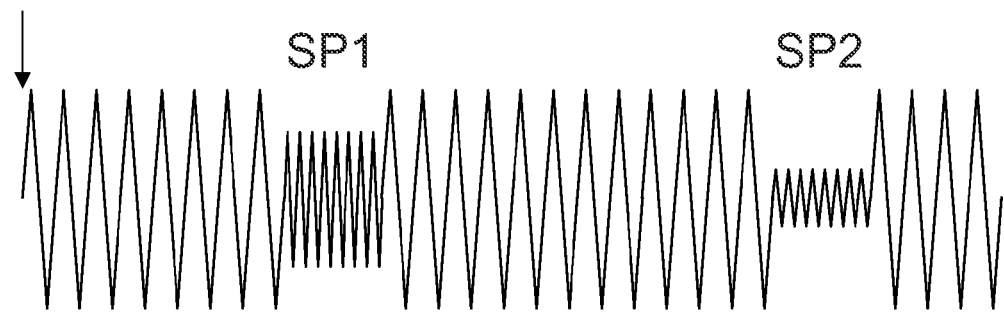

Referring now to FIGS. 4A-B, schematic drawings of examples of electromyographs (amplitude over time) of a masseter inhibitory reflex response measured at the masseter muscle are depicted. For purposes of example, FIG. 4A can be considered to represent a typical masseter inhibitory reflex response without concomitant occipital nerve stimulation, and FIG. 4B can be considered to be a representative possibility of a masseter inhibitory reflex response with concomitant occipital nerve stimulation in a subject in which there is a coupling of the occipital nerve and the trigeminal nerve or pathways associated therewith. The arrows shown in FIGS. 4A-B depict timing of application of a reflex-initiating stimulus to the mental nerve.

As shown in FIG. 4A, the masseter inhibitory reflex typically includes an early phase response (relaxation of the masseter muscle), SP1, and a later phase response (relaxation of the masseter muscle), SP2. It is believed that both the SP1 and the SP2 responses are indicative of a nociceptive trigeminal pathway (see, e.g., Jens Flinch, supra). Accordingly, changes in either of SP1 or SP2 (as a result of occipital nerve stimulation) may be useful in determining whether a subject would be a good candidate for occipital nerve stimulation for treatment of headache. Of course, even if the SP1 or SP2 response were not evoked by nociceptive input (and, it appears that the SP2 component bias some non-nociceptive aspects), they could still serve as useful diagnostic indicators of the presence or strength of occipital-trigeminal coupling.

In FIG. 4B, the amplitude of the early SP1 response is shown to be decreased to a lesser degree than the SP1 response in FIG. 4A. As discussed above, the response in FIG. 4B is an example of a response that might be seen with occipital nerve stimulation during the period of time in which the EMG response to the masseter inhibitory reflex is recorded. Such a decrease in amplitude of the SP1 response would be indicative of coupling between the occipital nerve and the trigeminal nerve or pathways associated therewith that may be predictive of whether the patient would be a good candidate for occipital nerve stimulation for treatment of headache.

FIG. 4B provides another example of a response that may be indicative of a subject being a suitable candidate for occipital nerve stimulation for treatment of headache, where the time of onset of the late SP2 response is delayed relative to that depicted in FIG. 4A. It will be understood that any suitable parameter (e.g., onset, duration, or amplitude) of any suitable characteristic aspect (e.g., SP1 or SP2) of the masseter inhibitory reflex may be employed for purposes of evaluating the existence or strength of coupling between the occipital nerve and the trigeminal nerve or pathways associated therewith or for determining whether a subject may be a suitable candidate for occipital nerve stimulation for treatment of headache.

Other trigeminal reflexes that may be tested or evaluated in the presence and absence of occipital nerve stimulation include the corneal reflex and the jaw-jerk reflex. The corneal reflex and the jaw-jerk reflex may be evoked and recorded in any suitable manner. For example, the corneal reflex response may be recorded via (e.g., in or near) the orbicularis oculi muscle. The jaw-jerk reflex may be evoked by applying a downward tap just below the lips of the subject, at the chin, while the subject's mouth is held slightly open, and the response may be recorded via (e.g., in or near) the masseter muscle. Both the jaw-jerk and the corneal reflexes are typically uni-modal in response and result in increased amplitude in the resulting EMG, due to muscle contraction. Changes in amplitude, onset, or duration of the EMG response with occipital nerve stimulation may be used to determine whether occipital-trigeminal coupling exists, the strength of the occipital-trigeminal coupling, or whether a subject may be a candidate for occipital nerve stimulation for treatment of headache.

Of course, any other suitable trigeminal reflex may be evoked and recorded in the presence and absence of occipital nerve stimulation in accordance with the teachings presented herein to determine whether occipital-trigeminal coupling exists, the strength of the occipital-trigeminal coupling, or whether a subject may be a candidate for occipital nerve stimulation for treatment of headache.

Figure 5A:
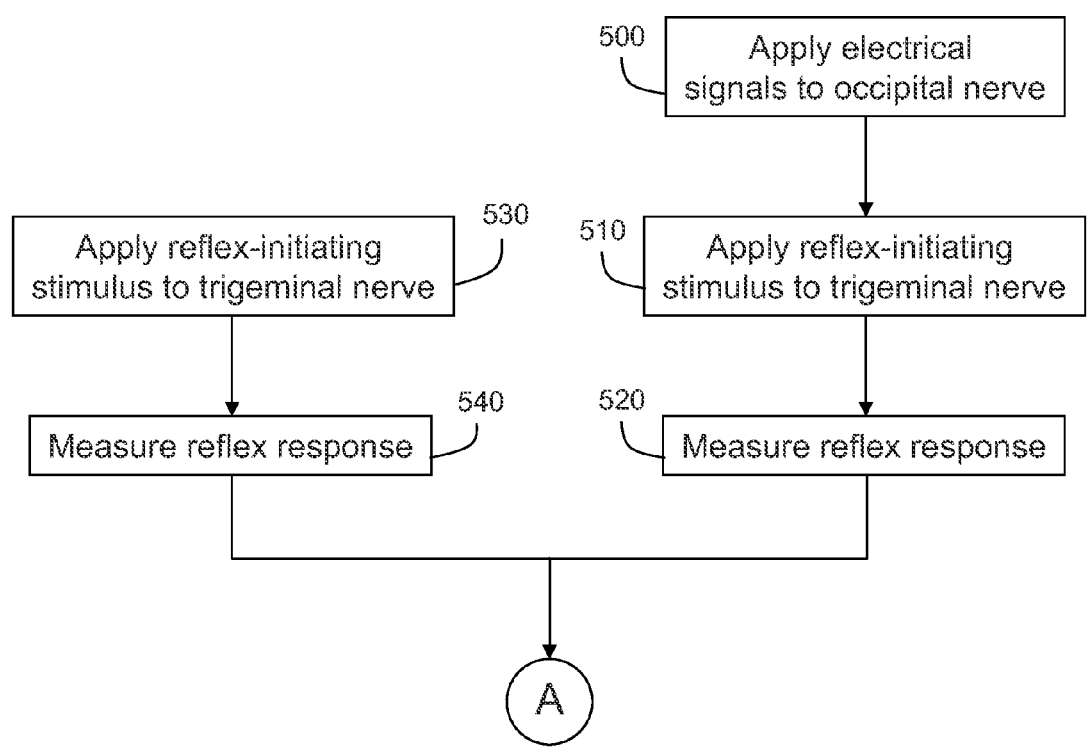
FIGS. 5A-C are flow diagrams of embodiments (B, C) of methods presented herein.
Figure 5B:
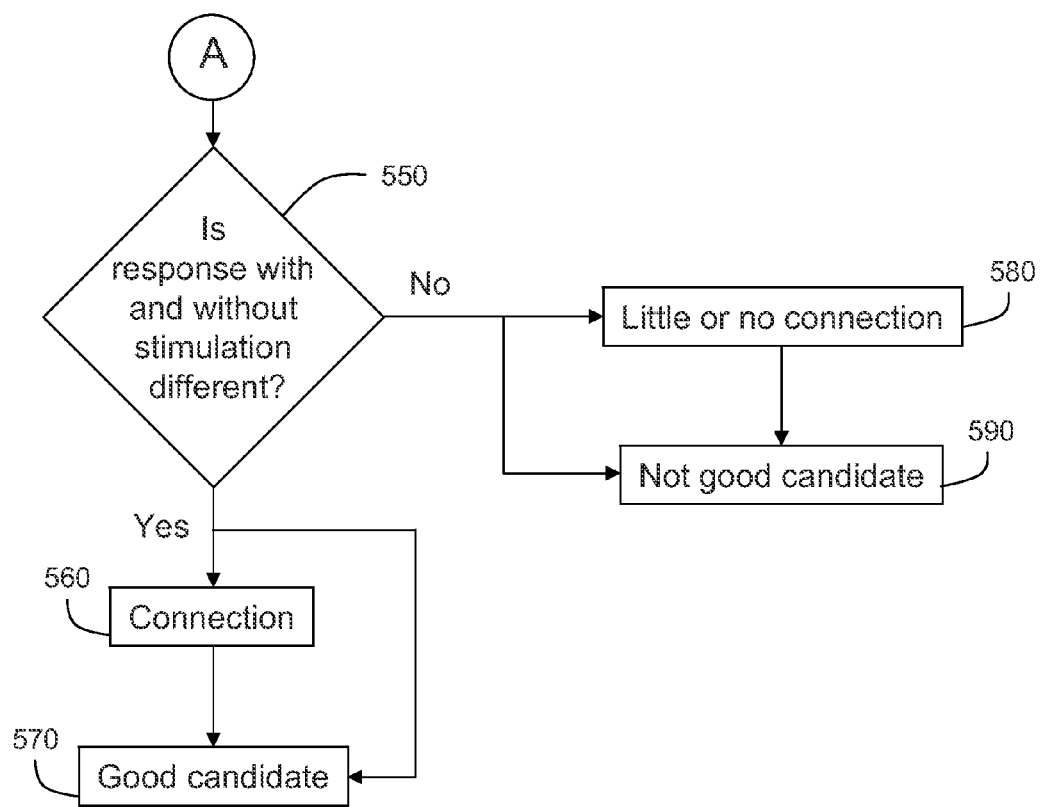
Figure 5C:
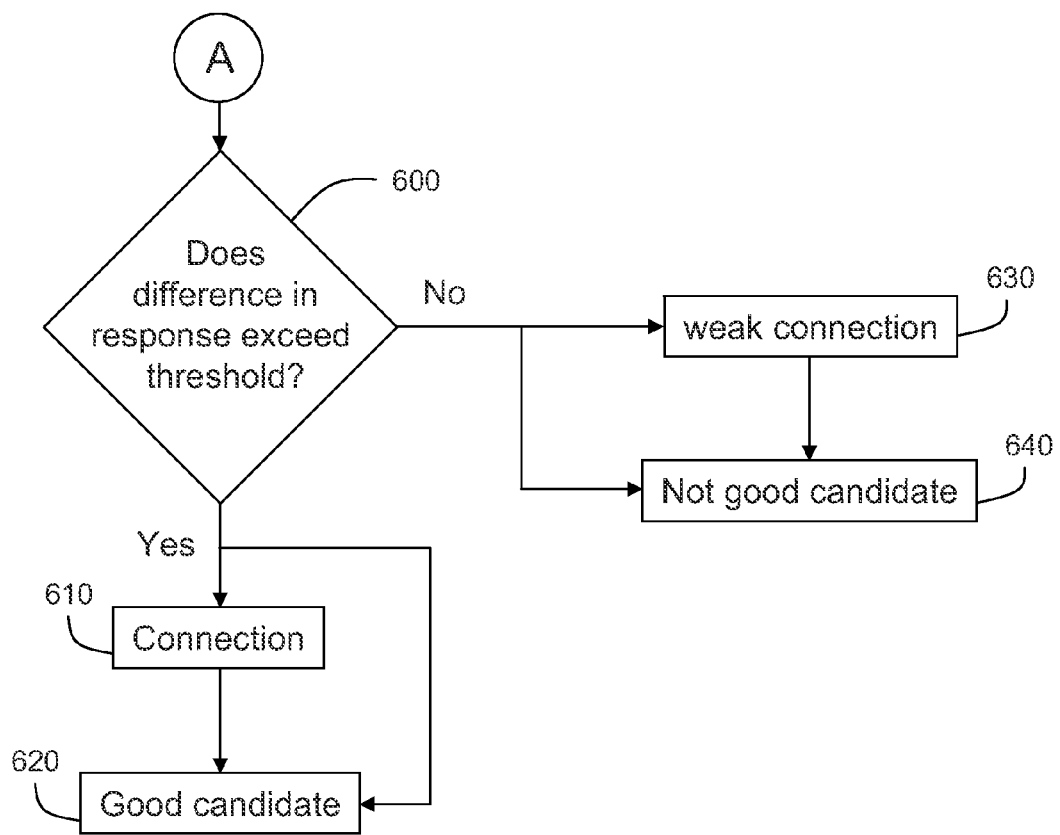

Referring now to FIGS. 5A-C, overviews of methods are illustrated. As shown in FIG. 5A, the methods include applying electrical signals to an occipital nerve of a subject (i.e., occipital nerve stimulation) (500), applying a reflex-initiating stimulus to an trigeminal nerve (510) during the time period of occipital nerve stimulation (ONS), and measuring or recording the trigeminal reflex response (520). As used herein, "the time period of ONS" refers to the time in which the ONS is actually applied and the time following actual application of ONS in which the previously applied ONS continues to affect a trigeminal reflex response. That is, the time period of ONS may last seconds, minutes, or days following the actual application of the ONS. In most cases a reflex response will be tested during the actual application of the ONS or within seconds or minutes (e.g., within 60 minutes, 30 minutes, 10 minutes, 5 minutes, or 1 minute of the end of the actual application of the ONS). The methods further include applying a reflex-initiating stimulus to the trigeminal nerve (530) during a period of time in which no electrical signals are being applied to the occipital nerve, and measuring or recording the trigeminal reflex response (540). It will be understood that the period of time in which no electrical signals are being applied to the occipital nerve is a period of time in which a prior application of ONS, if any, no longer has a significant effect on a trigeminal reflex response. As indicated in FIGS. 5B-C, the recorded responses in the absence and presence of occipital nerve stimulation may be compared to determine whether there is coupling between the occipital nerve and the trigeminal nerve or pathways associated therewith ("occipital-trigeminal coupling"), the strength of the occipital-trigeminal coupling, or whether a subject suffering from headache may benefit from occipital nerve stimulation.

Referring now to FIG. 5B, a method may further include determining whether a trigeminal reflex response is different in the presence occipital nerve stimulation (ONS) than in the absence of occipital nerve stimulation (550). As indicated above, the "presence" of ONS refers to the time period of actual application of ONS and the time following actual application of ONS in which the ONS continues to have an effect on a trigeminal reflex response. The "absence" of ONS refers to a period of time in which no actual ONS is being applied and in which there is no remaining significant effect on a trigeminal reflex response of previously applied ONS. If the response or a characteristic aspect of the reflex response is different in the presence and absence of ONS, a conclusion may be made that a connection exists between the occipital nerve and the trigeminal nerve or pathways associated therewith (560). Accordingly or alternatively, the subject may be considered a good candidate (570) for occipital nerve stimulation for treatment of headache. If there is no difference, then a conclusion may be made that there is little or no occipital-trigeminal coupling (580) or that the subject may not be considered a good candidate (590) for occipital nerve stimulation for treatment of headache.

Referring now to FIG. 5C, a method may further include determining whether a trigeminal reflex response, or an aspect thereof, in the presence occipital nerve stimulation is different from the reflex response, or aspect thereof, in the absence of occipital nerve stimulation by a predetermined threshold (600). For example, and as described above, a parameter (e.g., onset, amplitude, or duration) of a characteristic aspect of a reflex response may change by 10% or more, 15% or more, 20% or more, 25% or more or 30% or more when measured or recorded in the presence of occipital nerve stimulation relative to a corresponding parameter in the absence of occipital nerve stimulation. If the difference meets or exceeds a threshold, a conclusion may be made that a connection exists between the occipital nerve and the trigeminal nerve or pathways associated therewith (610). Accordingly or alternatively, the subject may be considered a good candidate (620) for occipital nerve stimulation for treatment of headache. If the difference does not meet or exceed the threshold, then a conclusion may be made that there is weak or no occipital-trigeminal coupling (630) or that the subject may not be considered a good candidate (640) for occipital nerve stimulation for treatment of headache.

It will be understood that it may be desirable to test the presence or strength of the occipital-trigeminal coupling in subjects suffering from headaches to determine whether the subjects may be candidates for occipital nerve stimulation. Accordingly, the methods described herein may include selecting or identifying a subject suffering from headache. Physicians or other health care professionals can readily identify headache and those subjects that may suffer from headache. For example, cluster headache is typically unilateral where the patient often experiences a stabbing or piercing pain in the eye or a pain as if someone were "pulling your eye out." The headache may be accompanied by a tearing or bloodshot eye and a runny nose on the side of the headache. It can radiate from the eye to the forehead, temple and cheek on the same side as the headache. The pain is often described as excruciating. By way of further example, migraine headache often begins as a dull ache and then develops into a constant, throbbing and pulsating pain that may be felt at the temples, as well as the front or back of one side of the head. The pain is often accompanied by nausea and vomiting, and sensitivity to light and noise. Migraine may occur with or without aura; i.e. a manifestation of a neurological symptom, which typically begins from five to thirty minutes before the onset of the headache. The aura can include vision hallucinations, such as "seeing" of wavy or jagged lines, dots or flashing lights, or tunnel vision or blind spots; hearing hallucinations; or disruptions in smell, taste, or touch. Of course, any other symptoms or diagnostic aids available to a physician or health care provider may be used to determine whether a person is a subject suffering from headache.

Those skilled in the art will recognize that the preferred embodiments may be altered or amended without departing from the true spirit and scope of the disclosure, as defined in the accompanying claims.

In the claims that follow, designators "first", "second" and the like are used for purposes of differentiation between two different events and do not necessarily mean that the "first" event must occur before the "second" event. For example, a "first" period of time may occur after a "second" period of time. Additionally, a "first" stimulus and a "second" stimulus may consist of the same parameters.

In the claims that follow, the period of time during which electrical signals are applied an occipital nerve is a period of time in which the electrical signals are actually being applied and the time following the actual application of the signals in which the ONS continues to affect a trigeminal reflex response. Similarly, a trigeminal reflex response that is measured in the "presence: of ONS may be measured following actual application of electrical signals to the occipital nerve.

It will be understood that the period of time during which no electrical signals are being applied to the occipital nerve is a period of time in which a prior application of ONS, if any, no longer has a significant effect on a trigeminal reflex response. Similarly, the "absence" of ONS refers to a period of time in which no actual ONS is being applied and in which there is no remaining significant effect on a trigeminal reflex response of previously applied ONS.

Typically, a trigeminal reflex response will be measured during the time of actual ONS or within seconds or minutes (e.g., within 60 minutes, 30 minutes, 10 minutes, 5 minutes, or 1 minute) following actual application of ONS.

What is claimed is:

1. A method comprising:
applying electrical signals to an occipital nerve of a subject during a first period of time;
applying a first reflex-initiating stimulus to a trigeminal nerve of the subject during the first period of time; and recording a first response of a muscle associated with a reflex evoked by the first reflex-initiating stimulus during the first period of time;
applying a second reflex-initiating stimulus to the trigeminal nerve of the subject during a second period of time in which electrical signals are not being applied to the occipital nerve; and recording a second response of the muscle associated with a reflex evoked by the second reflex-initiating stimulus during the second period of time; and
determining whether the application of the electrical signals to the occipital nerve affected the trigeminal reflex response, wherein the determining comprises comparing the first response to the second.

2. The method of claim 1, wherein the first and second reflex-initiating stimuli consist essentially of the same parameters.

3. The method of claim 1, wherein the first and second reflex-initiating stimuli are selected from the group consisting of electrical signals applied via a lead and heat applied via an infrared laser.

4. The method of claim 1, wherein the first and second reflex-initiating stimuli are configured to stimulate nociceptive neurons of the trigeminal nerve.

5. The method of claim 1, wherein the first and second reflex-initiating stimuli are applied to a supra-orbital nerve and are configured to evoke a blink reflex, and wherein the muscle associated with the reflex is an orbicularis oculi muscle.

6. The method of claim 1, wherein the first and second reflex-initiating stimuli are applied to a mental nerve and are configured to evoke a masseter inhibitory reflex, and wherein the muscle associated with the reflex is a masseter muscle.

7. The method of claim 1, wherein the first and second reflex-initiating stimuli are configured to evoke a corneal reflex, and wherein the muscle associated with the reflex is an orbicularis oculi muscle.

8. The method of claim 1, wherein the first and second reflex-initiating stimuli are configured to evoke a jaw-jerk reflex, and wherein the muscle associated with the reflex is a masseter muscle.

9. The method of claim 1, wherein the electrical signals applied to the occipital nerve are applied to a greater occipital nerve or a lessor occipital nerve.

10. The method of claim 1, further comprising identifying the subject as a headache sufferer.

11. The method of claim 10, wherein the subject suffers from migraine or cluster headache.

12. The method of claim 10, further comprising identifying the subject as a candidate for occipital nerve stimulation therapy if the application of the electrical signals to the occipital nerve are determined to have affected the trigeminal reflex response.

13. The method of claim 12, wherein recording the first and second responses comprises recording by electromyography (EMG) and wherein the subject is identified as a candidate for occipital nerve stimulation therapy if (i) an EMG amplitude of a characteristic aspect of the first response is decreased relative to the second response, (ii) a duration of a characteristic aspect of the EMG response is decreased in the first response relative to the second response, or (iii) an onset of a characteristic aspect of the EMG response is delayed in the first response relative to the second response.

14. The method of claim 13, wherein the subject is identified as a candidate for occipital nerve stimulation therapy if the EMG amplitude of the characteristic aspect of the response is decreased by 20% or more, the duration of the characteristic aspect of the response is decreased by 20% or more, or the onset of the characteristic aspect of the response is delayed 20% or more in the first response relative to the second response.

15. A method for determining a strength of modulation of a trigeminal reflex by occipital nerve stimulation in a subject suffering from headache, comprising:
identifying the subject suffering from headache;
applying electrical signals to an occipital nerve of the subject during a first period of time;
evoking a first trigeminal reflex in the subject during the first period of time, and recording a first response to the evoked first reflex;
evoking a second trigeminal reflex in the subject during a second period of time in which electrical signals are not applied to the occipital nerve, and recording a second response to the evoked second reflex; and
determining the strength of the modulation of the trigeminal reflex by the occipital nerve stimulation by comparing one or more parameters of a characteristic reflex response of the first recorded response to one or more parameters of a characteristic reflex response of the second recorded response.

16. The method of claim 15, further comprising selecting the subject as a candidate for occipital nerve stimulation therapy if the strength of the modulation meets or exceeds a predetermined threshold.

* * * * *